(12) United States Patent
Ding et al.

(10) Patent No.: US 7,993,677 B2
(45) Date of Patent: Aug. 9, 2011

(54) DENSITY-CONTROLLED PARTICULATE SUSPENSIONS FOR FOODSTUFF, COSMETIC, PHARMACEUTICAL AND OTHER USES

(75) Inventors: Li Ding, Castanet Tolosan (FR); Stephanie Morar, Toulouse (FR); David Schlossman, Short Hills, NJ (US)

(73) Assignee: Kobo Products, Inc., South Plainfield, NJ (US)

( * ) Notice: Subject to any disclaimer, the term of this patent is extended or adjusted under 35 U.S.C. 154(b) by 922 days.

(21) Appl. No.: 10/722,968

(22) Filed: Nov. 26, 2003

(65) Prior Publication Data

US 2004/0228886 A1    Nov. 18, 2004

Related U.S. Application Data

(60) Provisional application No. 60/429,816, filed on Nov. 27, 2002.

(51) Int. Cl.
*A61K 9/14* (2006.01)
*A61K 9/50* (2006.01)
*A61K 9/56* (2006.01)

(52) U.S. Cl. ......... 424/489; 424/492; 424/493; 424/494

(58) Field of Classification Search ................. 424/401, 424/489, 492, 493, 494
See application file for complete search history.

(56) References Cited

U.S. PATENT DOCUMENTS

| 3,334,052 A | 8/1967 | Kurz et al. | 252/316 |
| 6,319,507 B1 * | 11/2001 | Delrieu et al. | 424/401 |
| 6,852,266 B2 * | 2/2005 | Robinson et al. | 264/442 |

FOREIGN PATENT DOCUMENTS

| JP | 2000-290166 | 10/2000 |
| JP | 2001-524123 | 11/2001 |
| JP | 2002-020228 | 1/2002 |
| JP | 2002-508430 | 3/2002 |

* cited by examiner

*Primary Examiner* — Gina C Yu

(74) *Attorney, Agent, or Firm* — Handal & Morofsky, LLC

(57) ABSTRACT

Stable and uniform distribution of gel beads or other particulate material, dispersed in a liquid medium can be obtained by including a density-reducing agent within the gel beads to provide the particle with a desired bulk density, for example a density close to that of the disperse liquid medium. Suitable density control can prevent migration due to gravity leading to settling in storage. Gel beads formulated with agar are suitable for use in cosmetics and for inclusion in cosmetics formulating processes which may employ modestly elevated temperatures. Attractive and novel cosmetics bead suspensions are described. Additional to cosmetics, pharmaceutical, foodstuff and other applications are disclosed. Examples of suitable density-reducing agents include very low density hollow polymeric microspheres and temperature-sensitive expandable thermoplastic microspheres.

26 Claims, 3 Drawing Sheets

Density of Gel Beads with PG-Hydroxyethylcellulose Stearyldimonium Chloride sink float

| Sucrose (%) | | Water | 6 | 10 | 12 | 15 | 20 | Resultant Density |
|---|---|---|---|---|---|---|---|---|
| Density | | 0.997 | 1.0219 | 1.0381 | 1.047 | 1.06 | 1.081 | |
| Expancel (%) | 0 | | | | | | | |
| | 0.02 | | | | | | | 1.0381<d<1.047 |
| | 0.04 | H | | | | | | 0.997<d<1.0219 |
| | | B | | | | | | 0.997<d<1.0219 |
| | 0.06 | | | | | | | d<0.998 |

Figure 4

Density of Gel Beads containing Polyquaternium 11 sink float

| Sucrose (%) | | Water | 6 | 10 | 12 | 15 | 20 | Resultant density |
|---|---|---|---|---|---|---|---|---|
| Density | | 0.997 | 1.0219 | 1.0381 | 1.047 | 1.06 | 1.081 | |
| Expancel (%) | 0 | | | | | | | 1.047<d<1.06 |
| | 0.02 | | | | | | | 1.0381<d<1.047 |
| | 0.04 | | | | | | | 1.0219<d<1.0381 |
| | 0.06 | H | | | | | | 0.997<d<1.0219 |
| | | B | | | | | | 0.997<d<1.0219 |
| | 0.08 | H | | | | | | d = ~0.997 ? |
| | | B | | | | | | d = ~0.997? |
| | 0.1 | | | | | | | d<0.997 |
| | 0.12 | | | | | | | d<0.997 |

Figure 5

DENSITY-CONTROLLED PARTICULATE SUSPENSIONS FOR FOODSTUFF, COSMETIC, PHARMACEUTICAL AND OTHER USES

CROSS REFERENCE TO RELATED APPLICATIONS

This application claims the priority of U.S. provisional patent application No. 60/429,816, filed Nov. 27, 2002, the entire disclosure of which is hereby incorporated herein by reference thereto.

STATEMENT REGARDING FEDERALLY SPONSORED RESEARCH OR DEVELOPMENT (Not applicable.)

BACKGROUND OF THE INVENTION

The present invention relates to density-controlled particulate suspensions for foodstuff, cosmetic, pharmaceutical and other uses and their manufacture. More particularly the invention relates to gel beads suitable for dispersing or suspending in various media to provide, or for use in, foodstuffs, cosmetics, pharmaceuticals, nutraceuticals and the like and to the resultant dispersions or suspensions. Still more particularly, but not exclusively, the invention relates to such gel beads which have a visible appearance in relevant media, and especially to gel beads which convey a desired visual appearance such as color, pearlescence, sparkles, reflectivity, opacity or other visual effect to the media or end product formulation. Furthermore, the invention relates to such products and suspensions containing the inventive gel beads.

The invention will be described with particular reference, by way of example, to the formulation of gel beads as a cosmetic or dermatological delivery system having a variety of applications for delivery of topically applied active agents to the skin, to methods of preparing such delivery systems and to cosmetic or dermatological formulations in which the delivery systems may be incorporated. Based upon these disclosures, the use or application of the invention to other products such as foodstuffs or pharmaceuticals will be apparent to those skilled in the art.

Known to the art are many different types of gel beads made from polysaccharides, gelatin, or other suitable bead forming materials are used in gels and emulsions for their decorative effect and for encapsulation or entrapment of active ingredients.

Sweeny, U.S. Pat. No. 4,756,905 discloses a method of treating a surface (application of colored cosmetics to the human body, column 1, lines 10-11) with an active ingredient (encapsulated pigment, column 3, line 2) comprising providing a carrier liquid (e.g. the carrier liquid conventionally employed in a suntan lotion, column 2, line 61); dispersing in the carrier liquid a multiplicity of visible friable beads, each containing active ingredients for treating the surface (addition of microcapsules containing light-stable dyes or pigments, column 2, lines 62-64); and massaging the carrier with beads onto the surface for rupturing the beads and discharging the active ingredient to mark the surface with ruptured beads (light rubbing (as with a finger) will rupture the microcapsules, highlighting or changing the color in the area where the cosmetic was rubbed by exposing the encapsulated pigment within the composition, column 2 line 67 to column 3, line 3.)

Noda, U.S. Pat. No. 5,089,269 discloses a cosmetic composition on an external treatment agent containing microcapsules, with an average particle size of 0.1 to 2000 .mu.m, enclosing a hydrophobic component, wherein the microcapsules are composed of a gelatin film swollen with water.

Karassik, et al, U.S. Pat. No. 5,925,338 discloses a clear antiperspirant or deodorant gel composition which exhibits reduced staining while retaining aesthetic attributes and efficacy. The oil phase comprises about 10 to 25% of the composition and contains a silicone oil and a polyether substituted silicone emulsifying agent. The silicone oil comprises a mixture of a non volatile silicone, preferably a non-volatile linear silicone, and a volatile linear silicone. It has been found that reducing the amount of non-volatile silicone in the known gel composition to a relatively low level (e.g. below about 5%) and adding an amount of volatile linear silicone to the composition (e.g. above about 2%, preferably above about 5%) substantially improves the non-staining properties of the composition.

Ferguson et al. U.S. Pat. No. 6,045,813 discloses surface treatment compositions and methods for skin care and household use. The compositions contain rupturable, or friable beads containing an active ingredient, for example an antiseptic or fragrance. The active ingredient can mark the treated surface with ruptured beads and may be a colorant. The beads employ a diameter and thickness which avoid rupturing during the manufacture of a lotion or gel or the like containing the beads, and after an induction period incubating in the manufactured product are friable when rubbed on to the skin or dispensed through a restrictive orifice.

Delrieu, U.S. Pat. Nos. 5,961,990 and 6,319,507 ("the Delrieu patents") disclose protective cosmetic particulate gel delivery systems for a topically applied active agent employing an agar gel and a restraining polymer to retain the active agent in the gel. The particles have an average particle diameter of at least 0.05 mm while the restraining polymer has a molecular weight of at least 50,000 daltons and has retention groups to bind the active agent. The restraining polymers can be selected from the group consisting of polyquaternium 24, laurdimonium hydroxyethylcellulose, cocodimonium hydroxyethylcellulose, steardimonium hydroxyethylcellulose, quaternary ammonium substituted water-soluble polysaccharides, alleyl quaternary celluloses and polypeptides having or provided with retention groups to retain the active agent. They are soft enough for to be crushed on the skin without leaving any residue. They are stable in a wide range of pH and in formulations containing high concentrations of surfactants. The delivery system can be incorporated in multiphase cosmetic formulations such as gels, creams and lotions. These gel beads can be used for the decoration of formulas and the delivery of active ingredients.

Relatively large polysaccharide- and gelatin-based beads including, by way of example, some of the preferred embodiments of gel beads disclosed in the Delrieu patents, may be intended to have a distinct visual appearance in the end product. In contrast, the individual presence of smaller particles, such as powders and microspheres, in a given cosmetic formulation may not be detectable by the naked eye, and irregularities in their distribution may not be apparent. However, nonuniform distribution, such as settling or floating of visible beads intended to suspended in a clear liquid and packaged in a clear container is likely to be unattractive and may result in inconsistent delivery of useful ingredients transported in the visible beads.

There is accordingly a need for gel beads and comparable particles, and methods of making them, that can be provided in liquid dispersions with managed distribution of the beads or other particles in liquid media, and in particular for such products and methods that are suitable for cosmetics formulation.

The foregoing description of background art may include insights, discoveries, understandings or disclosures, or associations together of disclosures, that were not known to the relevant art prior to the present invention but which were provided by the invention. Some such contributions of the invention may be specifically pointed out below, whereas other such contributions of the invention will be apparent from their context.

BRIEF SUMMARY OF THE INVENTION

It is an object of the present invention to solve the problem of providing compositions and methods suitable for cosmetic, pharmaceutical and other uses which permit relatively uniform distribution of gel beads and other particles in suspensions, in a stable, long-lasting manner, and preferably also to provide an aesthetically desirable effect and an end product that is appealing to a consumer.

In one aspect the invention provides particulate material intended for dispersion in a liquid medium to provide a suspension, the particulate material comprising a plurality of particles dispersible in the liquid medium, the particles optionally each comprising an active agent wherein the particles are density-controlled, each particle comprising an effective quantity of a density-reducing agent within the particle to provide the particle with a desired bulk density.

Desirably, the quantity of density-reducing agent is sufficient to permit the particles to be uniformly and stably dispersed in the liquid medium or is sufficient to provide the particles with a density less than or equal to the density of the liquid medium or is from about 0.8 g/ml to about 1 g/ml. If desired, the density of the particles can be such that the particles can maintain a uniform distribution in the liquid medium when standing quiescent at about room temperature for a period of at least 1 month.

With advantage, the particulate material can comprise gel beads and the gel beads can have a visual property selected from the group consisting of visibility in the intended liquid medium, a transparent colored appearance, a transparent colored appearance and transparency in the intended liquid medium. In addition, or alternatively, the gel beads can comprise, or constitute, a cosmetic or pharmaceutical material intended for topical application to the skin, hair, nails, oral or other bodily cavity of a mammal.

In another aspect the invention provides a method of preparing density-controlled beads formed of bead material that is liquid at elevated temperatures, the method comprising admixing bead material ingredients at an elevated temperature, forming the resultant mixture into droplets or globules; and cooling the droplets or globules to form beads. The method comprises including in the bead material ingredients a density-control agent in a quantity sufficient to provide a desired gel bead density Some embodiments of the method comprise the elements of:
  a) dissolving a water soluble gelling agent, optionally agar, in water heated to a first temperature sufficient to dissolve the gelling agent, in a proportion of gel to water effective to form a gel at a lower temperature than the elevated temperature to form a first mixture;
  b) dispersing a density-control agent in water or oil at room temperature to form a second mixture;
  c) adding the second mixture to the first mixture to form a third mixture and then cooling the third mixture to an intermediate temperature above the gelling point of the first mixture; and
  d) discharging the cooled third mixture through a needle to form drops; and
  e) exposing the drops to a hydrophobic liquid maintained at a temperature below the first mixture's gelling point, whereby the drops are formed into gel beads incorporating the density-reducing agent.

In a further aspect, the invention provides a protective cosmetic particulate gel delivery system for a topically applied active agent, the delivery system comprising discrete, self-supporting gel particles of from 0.1 mm to 10 mm average size, the particles being insoluble in water at 25° C. and being formed of:
  a) a liquid medium having a density; and
  b) a plurality of particles dispersed in the liquid medium;
wherein the delivery system comprises:
  c) an effective quantity of a density-reducing agent dispersed within the particles to form density controlled particles wherein the density-reducing agent controls the density of the gel particles.

A still further aspect of the invention provides a density-controlled gel bead suspension suitable for human cosmetic, foodstuff or pharmaceutical use, the suspension comprising:
  a) a transparent liquid medium; and
  b) a plurality of visible gel beads dispersed in the liquid medium, the gel beads optionally being colored, wherein the gel bead suspension comprises:
  c) a density-reducing agent within the gel beads in a quantity effective to prevent gravitational migration of the gel beads in the liquid medium.

Other aspects of the invention provide a density-controlled bead suitable for dispersal in a transparent liquid medium to provide a suspension suitable for human cosmetic, foodstuff or pharmaceutical use, the gel bead comprising a structural bead material wherein the density-controlled beads comprise a density-reducing agent within the gel beads in a quantity effective to prevent gravitational migration of the gel beads in the liquid medium.

The invention also provides gel beads which have an enhanced visual appearance in suspension, for example a more uniform distribution in the liquid medium of visually perceptible beads. The inventive gel beads can be employed in cosmetic formulations having an improved efficacy and stability profile that allows for an extended shelf-life.

Preferred embodiments of the invention provide formulations which are chemically and visibly stable on the shelf but which can be effectively applied to a skin surface and, if present, release or deliver, an effective amount of an active ingredient topically or otherwise. Some embodiments of the invention provide a base composition which is capable of exhibiting improved aesthetics such as clarity and uniform suspension of gel beads in relatively low viscosity formulations. Further embodiments of the invention include a method for lowering the specific gravity of gel beads which having a higher specific gravity than that of the medium in which they are dispersed allowing the gel beads to remain suspended in low viscosity formulations without migrating towards the bottom of the container.

In addition, the invention relates to the suspension of beads within a low density medium to assure even distribution of said beads in the medium over an extended period of time providing for better efficacy and stability without compromising aesthetics. The beads may be gel beads or may be made of frangible material.

Thus, the present invention provides compositions and methods capable of maintaining gel beads and other such particles well dispersed in various formulations by controlling their density. Preferred embodiments provide precise control of the gel bead density enabling the gel beads or other particles to maintain a relatively uniform distribution without the beads settling out, even after relatively long periods of storage and even in relatively low viscosity media such as lotions, bath gels, shampoos, conditioners, and the like.

Preferably, the beads retain their desirable tactile properties when crushed and spread on the skin and also their processing and shelf stability. The inventive composition has desirable aesthetic capabilities of keeping gel bead suspended after the manufacturing process, though its shelf life until consumer purchase and beyond. The invention is particularly useful in suspensions where it is desirable to have colored or visibly opaque beads or microspheres uniformly distributed in a suspension where the suspension medium has a low viscosity relative to the gel beads. Where the suspended gel beads visually contrast with the medium, and particularly with a transparent or even clear medium, uniform distribution is highly desirable. In less viscous applications, even though the medium is possibly opaque or has the same appearance and refractive index as the beads so that they are invisible, uniform distribution is necessary for consistent delivery.

Desirably, the gel beads are pigmented to provide a visual contrast with the suspension medium, which is preferably substantially transparent so that beads on the far side of a typical consumer container are readily visible through the medium.

The invention is particularly advantageous in that it provides a means of producing gel bead or other particles in a range of densities for suspension in media of various densities. Thus the bead density can be selected according to the density of the intended dispersion medium.

The gel or other beads and suspensions of the invention can be employed in a wide variety of products including cosmetics, pharmaceutical, veterinary, food and agricultural products.

BRIEF DESCRIPTION OF THE DRAWINGS

Some embodiments of the invention, and of making and using the invention, as well as the best mode contemplated of carrying out the invention, if not described above, are described in detail below, by way of example, with reference to the accompanying drawings, in which like reference numerals designate the same or similar elements throughout the several views, and in which:

FIG. 4 is a chart showing the density of gel beads with PG hydroxyethylcellulose stearyldimonium chloride at different concentrations of density reducer; and FIG. 5 is graph showing the density of gel beads containing polyquaternium 11 at different concentrations of density reducer.

DETAILED DESCRIPTION OF THE INVENTION

Figure 1:
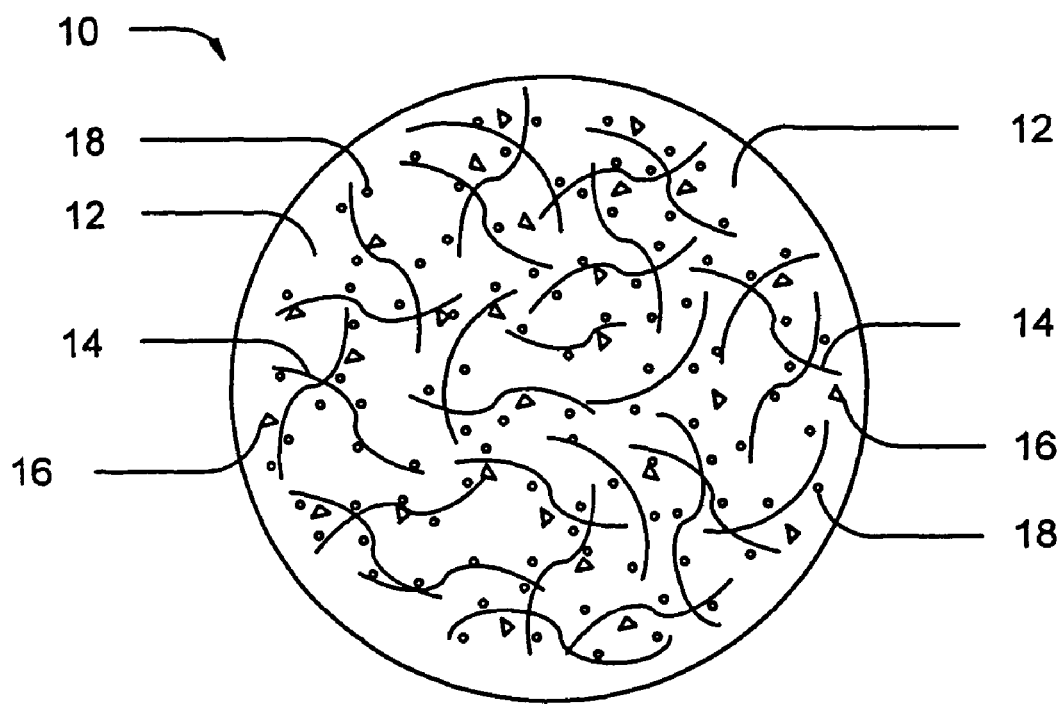
FIG. 1 is a schematic view of one embodiment of a density-controlled gel bead according to the invention.

Parts and proportions referenced in the following description, unless otherwise stated, or apparent from the context, are on a weight basis based on the weight of the relevant composition, a weight-for-weight basis.

Some useful embodiments of gel bead for employment in the invention can have compositions of ingredients with proportions by weight based on the weight of the composition which lie in the following approximate ranges:

| | |
|---|---|
| Gelling agent | about 0.5–5%, |
| Restraining Polymer | about 0.2–7.5% |
| Density reducer | about 0.02%–5% |
| Pigments | about 0.1–3% |
| Water quantity sufficient to 100% | |

In a preferred embodiment of the invention, the composition can be used to make gel beads which are preferably colored and visible spheres, which can be suspended in a low viscosity formula. In preferred embodiments, a retraining polymer is used to bind an active agent to the restraining polymer for retention within the gel beads. The restraining polymer can be anionic or cationic copolymer: such as alginate, polyquaternium-11 and so on. In order to adjust the density ratio of the gel beads to their suspension medium to be 1 or close to 1, low density microspheres can be used as a density-reducer. A preferred density reducer is EXPAN-CEL® expandable microspheres (product code 091 WE) which can be used to adjust the density of the beads.

Of particular interest as suspension or dispersion media for the inventive gel beads are multiphase cosmetic formulations such as gels, creams and lotions which include active ingredients such as antibacterial agents or essential oils, which are entrapped within friable beads, or microspheres. The gel beads of the invention can have a continuous gel phase throughout the bead in which expandable microspheres or other density control agent are distributed, or they can be capsule-like comprising a gel-like shell enclosing a liquid and/or solid component which can in turn comprise a hydrophobic or hydrophilic material, an oil-in-water or water-in-oil type emulsion or other material.

The invention enables gel beads to be effectively dispersed in low viscosity formulations by precisely controlling their density. The gel beads can still maintain their desirable tactile properties and their stability.

The invention is particularly applicable to relatively less viscous cosmetic lotions, creams and gels, shampoos and the like, although it can be beneficially employed in relatively more viscous formulations. Useful cosmetics products for employment in the invention include, without limitation, make up, foundation, and skin, nail and hair care products. Useful make-up products include products that deposit color or an opaque coating on the face, including foundation, blacks and browns, mascara, concealers, eye liners, brow colors, eye shadows, blushers, lip colors, and so forth. Useful foundation formulations include liquids, cremes, mousses, pancakes, compacts, concealers and similar products. Useful skin care products include products that moisturize, improve, or clean the skin. Useful skin, nail and hair care products include, but are not limited to, adhesives, toothpaste, anhydrous occlusive moisturizers, antiperspirants, deodorants, nail polish, solid emulsion compact, and hair conditioners.

Referring to FIG. 1, the density-controlled bead shown, whose structure is described in more detail below, comprises a colored gel bead 10 imparting color in a transparent or translucent liquid medium 11 containing an aqueous phase wherein gel bead 10 has a density relative to water of less than 1.0 or wherein the density ratio of gel bead 10 to the suspension medium 11 is less than or close to 1.

A particularly preferred embodiment of particulate cosmetic gel carrier comprises relatively small gel particles or beads 10 having an average particle size measured in millimeters. Particles 10 are small enough for cosmetic use, and preferably do not exceed 10 mm in diameter, on average, but not so small as to penetrate the skin or skin pores, no smaller than 0.1 mm. A preferred range of particle sizes is from about 0.5 to 3.0 mm in diameter, on average, with a more preferred range being from about 1 mm to about 2 mm. in diameter, on average.

Preferred methods of producing particles 10 yield a well-focused size distribution, so that at least 80 percent of particles 10, more preferably 90 percent of particles 10, lie within a desired average particle size bracket extending up to about 30 percent either side of a targeted average. If desired, for particular applications, a more uniform product can be obtained by mesh filtration.

One useful embodiment of gel bead 10, as is more fully described and claimed in the Delrieu patents, is a complex of a continuous phase of gel 12 in a self supporting solid or semi-solid form with an optional restraining polymer 14 and a density reducer 16. Dispersed randomly throughout each gel bead 10 is a water-soluble, preferably polar, restraining polymer 14, more preferably a quaternized cationic polymer, such as polyquaternium 24 or steardimonium hydroxyethylcellulose and density reducer 16. The preferred restraining polymer is polyquaternium 11. Restraining polymer 14 and density reducer 16 are entrapped in gel 12 so that they are not readily leached or otherwise released therefrom so long as the bead 10 retains its integrity.

Gel beads 10 can serve as a cosmetic delivery system for various active agents 18, for example ascorbic acid, lactic acid or papain, which may be bound to restraining polymer 14, or otherwise incorporated in the bead.

Alternatively, gel beads 10 can be employed without any further active ingredient, for example to deliver an entrapped restraining polymer, such as hyaluronic acid, a moisturizer, which has cosmetic or other active properties of its own. There are numerous possible alternative substances or materials to the preferred embodiments disclosed herein for gel 12, restraining polymer 14, density reducer 16 and active agent 18, some of which are set forth hereinbelow. Others will be apparent to those skilled in the art.

Some substances and materials usable in the practice of the invention are described in the following paragraphs. Others will also be apparent to those skilled in the art.

A particularly preferred gel-forming agent 12 for use in the practice of the invention is agar, also known as "agar-agar". Agar is insoluble when dispersed as a dry solid in water at low temperatures, however, it becomes soluble when heated to temperatures over 70-90° C. and forms a gel upon cooling. Agar is relatively expensive in comparison with some other commonly used gelling agents, but is particularly well suited for formulation with cosmetic vehicles, especially two-phase creams, gels and lotions which are usually homogenized at an elevated temperature. Gels are stable to both pH and moderate elevation of temperature.

Other such possible gels will be known or apparent to those skilled in the art. Such other gels should be capable of forming dimensionally stable, self supporting gel-polymer complex particles that are stable under the conditions of formulation, if any, (particles 10 themselves can constitute the end product), packaging and storage, and which can be crushed, spread or otherwise dispersed on the skin or nails of an end user to increase the surface area of particles 10 and disperse contained active in situ. The gel beads are preferably not unduly tacky and do not adhere to one another on contact. Preferred gels are water-soluble polymers that are pH stable. Such preferred gels can include: synthetic polymers, such as vinyl or acrylamide polymers, or copolymers; natural polymers, for example polysaccharides, or proteins or synthetically modified ones of such polymers; botanically derived gels; and can include gelling agents such as carbopol, a common, low-cost petroleum-derived, cosmetic gel.

However, in preparing gel beads 10 or formulating them into cosmetics, care should be taken to avoid exposing heat-sensitive agents to excessive heat, by adding them at lower temperatures, adding gel beads to cosmetic formulations after emulsification or by exposing gel beads containing such heat-sensitive actives for only short periods of time insufficient to be damaging.

It is to be understood that the gel-forming agent 12 selected for use in the practice of the invention desirably not only satisfies the particle or bead forming requirements described herein, but can also meet other requirements associated with the intended cosmetic, pharmaceutical, medicament, or other end use of the bead.

In a preferred embodiment of the invention, a restraining polymer 14 having a sufficient molecular weight to prevent egress of restraining polymer 14 from the gel, and having retention groups to bind the active agent to restraining polymer 14 for retention in the gel particles, is employed. Preferably also, restraining polymer 14 is sufficiently water-soluble that a desired proportion of the polymer can be co-dissolved with gel in an initial particle-forming step. Restraining polymer 14 used is preferably selected according to the desired active agent or agents to have one or more retention groups which will bind the active agent.

The invention is particularly useful in suspensions where gel beads 10 are colored or visibly opaque. Where the suspended gel beads visually contrast with liquid medium 11, for example with colored or opaque beads dispersed in a transparent or clear medium, a reasonably uniform spatial distribution of the beads in the disperse medium, which is preferably maintained throughout the shelf life of the product, is desirable. Conventional alternatives lacking the density control of the present invention wherein the beads settle or float, possibly aggregating into clusters at the bottom or top of liquid medium 11, provide an unattractive appearance and inefficient delivery of the bead-medium product.

Even where liquid medium 11 is opaque or has a similar appearance and refractive index to gel beads 10 so that they are more or less invisible, uniform distribution can still be desirable for consistent delivery of contained active ingredients to the skin or other surface.

Density reducer 16 can comprise a low density filler dispersed throughout each individual gel bead to adjust the density ratio of gel beads 10 to suspension medium 120 to a desired value, for example close to 1 or lower than 1. One embodiment of suitable density reducer 16 comprises small hollow particles or microspheres that contain a suitable gas, for example air, within a spherical shell. The hollow particles may be of fixed or variable volume to provide a specific or adjustable means of controlling the bead density. One useful embodiment of density reducer 16 comprises temperature-sensitive expandable thermoplastic microspheres whose final volume and density can be controlled during processing by suitable temperature management. Some useful materials from which the density controlling microspheres or other particles useful in the practice of the invention can be formed include phenolic materials, glass, ceramic, silica, PMMA and other suitable materials as will be known to those skilled in the art.

Density reducer 16 can comprise any suitable proportion by weight of gel bead 10 to provide a desired density adjustment as may be readily calculated. Because many suitable density reducers 16 are themselves of low density, and may commonly be described as being very light in weight, quite small proportions by weight can be effective to provide a desired density adjustment. For example, density reducer 16 can comprise from about 0.02% to about 5%, preferably less than 1% and more preferably from about 0.02% to about 0.1% by weight of gel bead 10. In one embodiment of the invention sufficient density reducer 16 is employed to adjust the relative density of gel beads 10 to be close to 1 or a little lower than 1. The particular final bulk density of gel beads 10 can be selected with reference to the density of the intended dispersion medium 11 and is preferably such as to permit gel beads 10 to spatially distribute evenly throughout dispersion medium 11 and to remain evenly distributed throughout a desired shelf life.

In an alternative embodiment of the invention, where a different spatial and visual effect is desired, sufficient density reducer 16 of a suitable density is employed to cause all or substantially all gel beads 10 to float at or near the surface of dispersion medium 11 and to readily regain a floating state after mixing e.g. by shaking.

Unless the context indicates otherwise, the densities referenced herein are relative densities or specific gravities, which is to say they are related to the density of water, 1 g/ml under standardized conditions. Thus, the density of many useful low viscosity formulations is close to 1, while other formulations, for example those containing a high or significant proportion of oil may be less than 1 Suitable fillers can be employed, pursuant to the invnention, to maintain the density ratio of the gel beads or other particles to the suspension medium within a desired range, for example, as described hereinbelow.

The size of density reducer 16 can desirably be significantly smaller than the size of gel beads. Preferred fillers have an average particle size less than about 20-100 microns.

In many embodiments, average particle size preferably should be less than 50 microns, and more preferably about 10 microns. Density reducer 16 should also be durable enough to withstand processing and use. Thus, a suitable density-reducing density reducer 16 consists of particles having an average particle size of less than about 100 microns, whose volume consists of a substantial percentage of gas.

Powders of thermoplastic synthetic material in the form of hollow microspheres, which can be obtained in particular by known processes. The hollow parts of these microspheres contain gas such as a hydrocarbon, air, or any other appropriate gas. The hollow microspheres can be made of any thermoplastic material that is nontoxic and nonirritating to the skin, for example polymers or copolymers of ethylene derivatives (in particular polyethylene, polystyrene, vinyl chloride acrylonitrile copolymers), polyamides, polyesters, urea-formaldehyde polymers, or vinylidene chloride copolymers (in particular vinylidene chloride and acrylonitrile copolymers). These hollow microspheres are very light: their specific gravity can be on the order of 0.01 to 0.1 $g/cm^3$, for example. As density-reducing fillers, hollow microspheres are superior to solid microspheres because microspheres entrap gas within the structure of each particle. While microspheres are limited by the density of the native material, microspheres can be prepared with densities much lower than the native material because a substantial portion of the volume of each microsphere is gas. Further, unless the microspheres are ruptured, the gas remains entrapped and the density of the microspheres, and correspondingly the product, does not increase with use.

In a preferred embodiment, the density-reducing filler comprises hollow plastic microspheres. Typical plastic microspheres exhibit relatively low density and high resilience. Many are irregular in shape, which promotes bonding and integration of components within the product.

A preferred density-reducing material comprises gas-filled thermoplastic microspheres available under the trademark EXPANCEL from Nobel Industries, Sundsvall, Sweden. EXPANCEL® expandable microspheres are available in expanded and unexpanded forms. The expanded microspheres have typical densities of 0.03 to 0.06 g/cc. The final density of the unexpanded microspheres can be varied by manipulating the processing conditions to cause different degrees of expansion. Depending on the selected processing conditions, the density can range from 1.2 g/cc, the density of the unexpanded microspheres, to <0.02 g/cc, the minimum density. The average particle size of the expanded microspheres can range from 25 to 75 micron, and typically is 50 micron. Low density microspheres such as EXPANCEL® expandable microspheres can be used as a density-reducer. In preferred embodiments, EXPANCEL® 091 WE is used to adjust the density of the microspheres. The preferred EXPANCEL® 091 WE product is already pre-expanded and has a size of 35-55 micron and a density of 24 $kg/m^3$.

Other suitable low density hollow microspheres that can be employed in the practice of the invention include for example, POLYTRAP (Dow Corning), silicone resin microspheres, (for example TOSPEARLS from Toshiba), precipitated calcium carbonate, magnesium carbonate, magnesium hydrocarbonate, hydroxyapatite, hollow silica microspheres (Silica Beads from Maprecos), glass microcapsules, and ceramic microcapsules.

However, more preferred alternatives to the EXPANCEL® product are other thermally expandable microspheres such for example as are disclosed in U.S. Pat. No. 5,834,526 to Wu, et al., U.S. Pat. No. 3,615,972 to Morehouse, et al., U.S. Pat. No. 4,108,806 to Cohrs, et al., U.S. Pat. No. 5,429,869 to McGregor, et al., PCT Publication No. WO 93/00390 to 3M Corporation and EP 559254A1 as well as several types of inorganic and organic lightweight filler such as hollow microspheres made from siliciceous material such as borosilicate material (such as the material disclosed in Miller et al, U.S. Pat. No. 5,534,348), ceramic, glass, or mineral, hollow particles made from film-forming plastic material including cellulose derivatives, thermoplastic synthetic resins, polystyrene particles, polypropylene spheres, polymeric beads, pearlite, vermiculite, hollow glass spheres, lightweight expanded geologic materials, and the like.

Those skilled in the art will understand that such optional additional compounds should be selected and employed in amounts such that the advantageous properties of the composition according to the invention, as described herein are obtained.

While, the invention does not require the delivery of an active agent 18 in gel beads 10, the invention is particularly advantageous in use with suspensions of microspheres that contain active agents as filled microspheres are often more dense than their suspension medium. Some examples of classes of dermally active, or dermally effective substances having biological or cosmetic activity, which can be topically delivered employing the delivery systems of the invention include: antioxidants including botanically derived polyphenols, for example procyanidin oligomers; free radical scavengers; topically active enzymes, for example, antibacterials, such as glucose oxidase, antioxidants such as superoxide dismutase, and proteolytic enzymes such as bromelain and papain, (useful for enzyme peeling); other enzymes such as the DNA repair enzymes described above; exfoliative retinoids, such as retinol and retinol esters including retinol acetate, vitamin A palmitate; purified plant extracts and plant proteins; vegetable oils, for example, grape seed, sunflower, safflower and jojoba oil; essential fatty acids, such as linoleic acid, linolenic acid and arachidonic acid; animal proteins, for example collagen, elastin and keratin; moisturizers, such as hyaluronic acid and other glycosaminoglycans; whitening agents such as arbutin; ultraviolet light filters; coated or uncoated organic and inorganic pigments such as titanium, zinc, and iron oxides and anti-actinic suspensions or dispersions of such inorganic oxides; melanin or a sepia ink extract; other colorants or dyes, and perfumes.

In addition, the gel wall material 12 can contain a harmless non-toxic colorant which is water soluble or water disbursable and which adds to the effect of the invention by providing a visual que to the amount of active ingredient being worked into the skin and also the fact that sufficient mechanical massaging has taken place to activate the ingredients by rupturing the microspheres and smearing to color. Conventional cosmetic formulations, with or without a predominant coloration in the composition, can be rendered colored, can be highlighted, or can be altered in color by the application of pressure to the composition after or during application. The presence within the composition of frangible microcapsules containing light-stable dyes or pigment enables this coloring phenomenon to occur. Color adjustable cosmetic compositions can comprise a first colorant, a binder, and a frangible microcapsule comprising a shell, an encapsulated liquid and a second light-stable colorant which differs in color from said first colorant.

While pigments and perfumes can have a role in enhancing the aesthetic appeal of the carrier microspheres in which they are incorporated, they can also perform cosmetic functions when the microspheres are applied to the skin or other endogenous surfaces, for example, the nails or hair and then crushed, commencing controlled release of the actives. The release can, to some extent, be user controllable. Thus, for example, a user can firmly spread a body cream containing perfume-loaded gel complex microspheres according to the invention, until they detect enough perfume is released or a rouge, makeup, foundation or other pigmented cosmetic, until the color is to their liking. The carrier microspheres and the respective proportions of their components can be adjusted to provide continued release to sustain the color or perfume intensity. In addition, the user can, with small, hard-to-see gel beads, refresh the active by further crushing and spreading residual uncrushed gel beads, at a later time.

In general, any active can be used that binds satisfactorily to restraining polymer 14 and can be released by contact with the skin. Many novel formulations and enhancements of known cosmetics that can be obtained by supplementing them with labile actives carried within and protected by the polymer-gel complex beads of the invention, will be apparent to those skilled in the art. One such product comprises a mixture of actives providing a novel prophylactic and therapeutic treatment for solar exposure comprises an ultraviolet absorbent or screening agent, for example titanium dioxide, an antioxidant, for example vitamin E, and a DNA repair enzyme, incorporated into gel-polymer complex beads, according to the invention. If desired, a melanocyte stimulant could be included. Such gel beads could be used per se, or incorporated into traditional creams or lotions.

Whether for aesthetics or function, it is also desirable to maintain a spatially uniform distribution of the gel beads in the suspension medium over a long period of time, preferably sufficient to account for the time from manufacturing, through packaging, distribution, sales, consumer purchase, and then finally use by the end user who can be different from the consumer. This is a period which can easily extend over months or even years.

Figure 2:
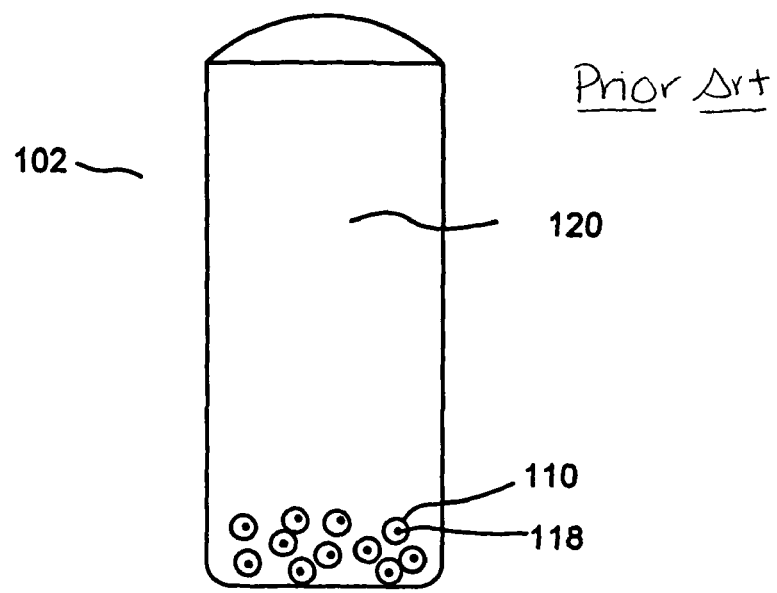
FIG. 2 is a view of a prior art shampoo containing relatively dense gel beads that have settled out.

Referring to FIG. 2, a bottle 102 of shampoo containing from about 1 to about 8% by volume of colored translucent prior art gel beads 110 containing botanical extracts 118 dispersed in a somewhat less dense liquid shampoo medium. The shampoo may have been presented as a gift and not used for another year or even as much as two years. Prior to the gift occasion bottle 102 may have been sitting on a store shelf for months and in a warehouse for even longer, so that the time from the final manufacturing step to user access could be several years. As shown, beads 110 while initially suspended in the shampoo 120 have settled through the liquid under their own weight. If the end user then finds a clear shampoo 120 with colored mass of gel beads 110 clumped at the bottom of the container, she may not use the shampoo and will have a negative image of the brand and possibly the manufacturer. Furthermore, were the consumer to use the product she may not get the benefit of the botanicals 118 in gel beads 110 which are at the bottom of the container and thus may be disappointed with the product 102. Clearly, maintaining a more uniform distribution of gel beads 110 in the suspension medium 120 over an extended period of time such as months or years, would be desirable.

To maintain uniform distribution, the gel bead density should be sufficiently close to that of the suspension medium to avoid gravitational migration, either up or down, preferably even after prolonged periods of storage. For this or other purposes, the density ratio of the gel beads to the suspension medium can be controlled to be close to 1 or slightly lower than 1, for example in the range of from about 0.98 to about 1 or possibly a lower value for example in the range of from about 0.95 to about 1. However it is believed desirable for uniform distribution that the bulk density, or apparent density in the suspension medium of the dispersed gel beads or other particles be as close as practicable to that of the suspension medium, for example, within about 1 percent.

However the density control afforded by the present invention enables a wide range of density reduction for example to relative density of 0.9 or even 0.8, if desired, or to any desired value between about 0.8 and about 1. Such relative densities, in relation to the use of water as a suspension medium, imply actual bulk or apparent densities of gel beads 10 in the range of about 0.8 g/ml to about 1 g/ml, although it will be appreciated that actual densities in excess of 1 g/ml may be useful for uniform distribution in aqueous media having densities greater than 1, or for other purposes. Such lower actual densities of gel beads 10, or other particles, may be useful for dispersion in non-aqueous media such as lipid or silicone fluids or emulsions. It will be understood that gel beads 10 can have any desired density within the physical capabilities of available materials, that serve a useful purposes and that the foregoing figures are intended merely to be illustrative.

Figure 3:
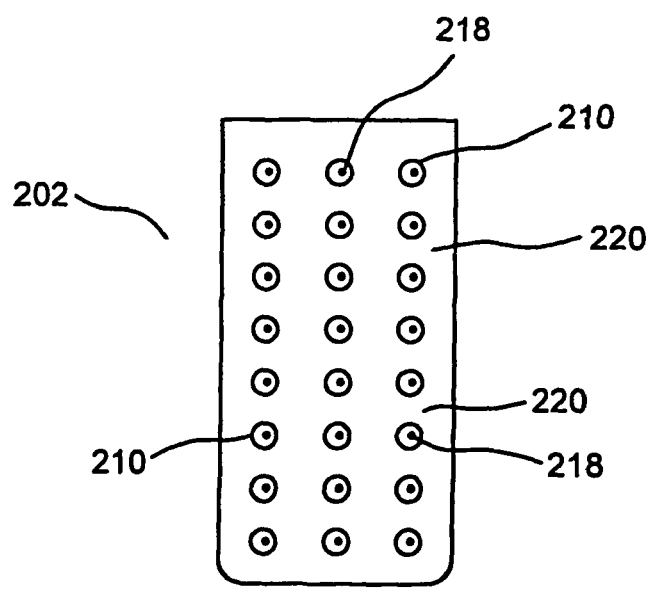
FIG. 3 is a view of a number of the gel beads illustrated in FIG. 1 uniformly distributed in a low viscosity formulation.

Referring to FIG. 3, bottle 202 of shampoo contains colored, suspended gel beads 210 comprising a density reducer suspended in shampoo 220. Gel beads 210 have a density that is close to or slightly less than the density of shampoo 220. In other words the density ratio of gel beads 210 to shampoo 220 is less than or close to 1. Gel beads 210 containing botanical extracts 218 are uniformly suspended in suspension medium 220 for a long period of time thus enhancing both the commercial potential and the efficacy of active agents 218. The invention adds a density reducer in the manufacturing process to produce a less dense product.

Some basic steps of one embodiment of a method of production of a preferred embodiment of the inventive gel beads and suspensions are as follows:

I. Dissolving a water soluble gelling agent, for example agar, in water heated to a temperature sufficient to dissolve the gelling agent, for example 90° C.;
II. Dispersing a water-soluble restraining polymer and a density reducer in water at room temperature, then mixing with pigment which is previously pre-dispersed in water;
III. Adding the phase II mixture into the phase I solution, then cooling the mixture to 45° C.; and
IV. Injecting the product of step III through a needle into a hydrophobic liquid maintained at 5 to 10° C. to further cool the mixture and form gel beads.

An ingredient to be encapsulated can be added in the phase II. The size of the gel beads can be controlled by the speed of oil flow or the needle diameter. In order produce gel beads more homogeneously, it is better to pre-disperse the density reducer in oil and then added in phase II.

Some non-limiting examples of the practice of the invention will now be described by way of illustration.

In Examples 1-7 described hereinbelow, the following materials can be used to form gel beads 10:

| | | |
|---|---|---|
| polysaccharide: | agar gel | (OSI, France) |
| restraining copolymer: | polyquaterium 11 or PG-hydroxyethylcellulose stearyldimonium chloride | (GAFQUAT 755N-PP from Quarrechim) (CRODACEL QS from Croda, Inc) |
| oil: | sunflower (*Helianthus annus*) seed oil | (FLORASUN 90 from Floratech) |
| pigment: | ultramarine blue | (Kingfisher) |
| density-reducer: | expandable microspheres | EXPANCEL ® |
| distilled water. | | |

Formulation:

The following formulation can be employed in the examples described below, as appropriate:

| | |
|---|---|
| I. Agar | 1.5% |
| Distilled Water | 50% |
| II. Polyquaterium 11 or PG-hydroxyethylcellulose stearyldimonium chloride | 7.5% |
| Sunflower Seed Oil (if used) | 2% |
| EXPANCEL ® expandable microspheres x = 0; 0.02; 0.04; 0.05; 0.08; 0.1 | x % |
| Ultramarine Blue | 0.5% |
| Distilled water | qsp 100% |

General Procedure:

The following general procedure can be employed in the examples described below, as appropriate:
I. 15 g of gel is dispersed in 500 g of water and the mixture is heated to 90° C. while stirring until the gel is completely dissolved to form a first mixture.
II. x g of EXPANCEL® expandable microspheres which may or may not be pre-dispersed in sunflower oil is added into a solution containing 75 g of restraining polymer, 5 g of ultramarine and about 380 g of water under agitation until the mixture is homogenous to form a second mixture.
III. The second mixture is added to the first mixture to form a third mixture and the temperature of the third mixture is cooled to 45° C. Then the cooled third mixture is injected to a paraffin oil bath to form gel beads.

Example 1

Preparation of Low Density Gel Beads with EXPANCEL® Expandable Microspheres and PG Hydroxyethylcellulose Stearyldimonium Chloride 1.5 g of agar is added to 50 g of distilled water and heated to 90° C. to form a first solution (I). In a separate container, 0.1 g of EXPANCEL® WE expandable microspheres, 0.5 g ultramarine blue and 7.5 g of PG hydroxyethylcellulose stearyldimonium chloride are dispersed in 40.4 g of water at room temperature to form a second solution (II). Then the second solution (II) is added into the solution of agar (I) which becomes a clear and translucent mixture (III) at room temperature. When the mixture (III) is cooled down to 45° C., it is injected by a peristaltic pump into a cold paraffin oil bath at 5° C. The gel beads are then formed and washed with water. The gel beads obtained float in water, demonstrating that they have a density lower than 1.

Example 2

Preparation of Low Density Gel Beads with EXPANCEL® Expandable Microspheres Pre-Dispersed in Oil 1.5 g of agar is added to 50 g of distilled water and heated to 90° C. to form a first solution (I). 0.1 g of EXPANCEL® WE expandable microspheres are pre-dispersed in 2 g of sunflower seed oil. Then, 0.5 g ultramarine blue and 7.5 g of PG hydroxyethylcellulose stearyldimonium chloride are dispersed in 38.4 g of water at room temperature and mixed with the oil mixture to form a second mixture (II). The preparation steps then follow the procedure of the previous example. The gel beads obtained have a density lower than 1 because they floats in water.

Example 3

Preparation of Low Density Gel Beads with Various Concentration of EXPANCEL® Expandable Microspheres Pre-Dispersed in Oil Following the procedure of example 2, EXPANCEL® WE expandable microspheres are pre-dispersed in sunflower seed oil. The gel beads are prepared using respective aliquots of 0.12%, 0.08%, 0.06%, 0.04%, 0.02%, and 0.00% of EXPANCEL® expandable microspheres.

Density testing on the prepared gel beads shows the following:

| % of EXPANCEL ® expandable microspheres | Density | Observation |
|---|---|---|
| 0.12% | <1 | The gel beads float in water |
| 0.08% | <1 | The gel beads float in water |
| 0.06% | <1 | The gel beads float in water |
| 0.04% | ~1 | Some of the gel beads float in water while some of the gel beads sink in water |
| 0.02% | >1 | The gel beads sink in water |
| 0.00% | >1 | The gel beads sink in water |

Example 4

Preparation of Low Density Gel Beads with EXPANCEL® Expandable Microspheres Pre Dispersed in Oil Using Polyquaterium 11

0.1 g of EXPANCEL® WE expandable microspheres is pre-dispersed in 2 g of sunflower seed oil. Then, 0.5 g ultramarine blue and 7.5 g of Polyquaterium 11 are dispersed in 38.4 g of water at room temperature and mixed with the oil mixture to form a second mixture (II). The preparation steps are then the same as the previous example. The density of these gel beads is low 1 because it floats in water.

Example 5

Preparation of Low Density Gel Beads with Various Concentration of EXPANCEL® Expandable Microspheres Pre-Dispersed in Oil Following the procedure of the previous example, Expancel WE is pre-dispersed in sunflower seed oil. The gel beads are prepared using 0.08% or 0.06%, 0.04%, 0.02% of Expancel.

Density testing on the gel beads shows the following:

| % of Expancel | Density | Observation |
| --- | --- | --- |
| 0.08% | <1 | The gel beads float in water |
| 0.06% | <1 | The gel beads float in water |
| 0.04% | ~1 | Some of the gel beads float in water while some of the gel beads sink in water |
| 0.02% | >1 | sink in water |

Example 6

Determination of Density of Gel Beads Using Sucrose Solution

Seven concentrations of sucrose solutions are prepared with the density of each solution measured according to Merck index. The gel beads are placed into the solutions of different sucrose concentrations. Where there is an even dispersion of the gel beads in a solution, the density of gel beads will be the same as the density of the sucrose solution. The densities of the solutions are as follows:

| % of sucrose in water | density |
| --- | --- |
| 3% | 1.0113 |
| 6% | 1.0219 |
| 8% | 1.0309 |
| 10% | 1.0381 |
| 12% | 1.047 |
| 15% | 1.06 |
| 20% | 1.081 |

By comparing the density of the gel beads against the densities of the various sucrose solutions, a more accurate density reading could be taken. FIG. 4 is a graph showing the Density of Gel Beads with PG-Hydroxyethylcellulose Stearyldimonium Chloride at different concentrations of density reducer; while FIG. 5 is a graph showing the Density of Gel Beads containing Polyquaternium 11 at different concentrations of density reducer.

The size of the gel beads themselves in a preparation can depend upon the active agent contained therein and/or the intended target. Sizing of gel beads according to the present invention can be carried out according to methods known in the art, and taking into account the active agent contained therein and the effects desired. A preferred embodiment of the present invention is a gel bead small enough for cosmetic use, and preferably not exceeding 10 mm in diameter, on average, but not so small as to penetrate the skin or skin pores. A minimum diameter, on average, is about 0.05 mm. (50 microns). A preferred range of particle sizes is from about 0.1 to 3.0 mm. in diameter, on average, with a more preferred range being from about 0.25 mm. to about 1 mm. in diameter, on average.

The above examples employ some of the procedures and materials of the formulas disclosed in the Delrieu patents which are fully incorporated herein by reference thereto. Other gel bead formulations can be utilized with the inventive method. Companies such as Lipo Chemicals (US), Lipothec (Spain), Ones (Korea), Coletica (France), and Hallcrest (UK) make suitable gel bead formulations.

The beads can be made by techniques known to those skilled in the art. Those skilled in the art will also appreciate that when the dispersions are made care is to be taken to avoid contamination. Other ingredients can also be added to into the mix at (II) and can be selected from the group consisting of: (1) water, as a moisturizing agent; (2) drying agents; (3) emulsifiers (emulsifying agents), (4) emollients; (5) humectants; (6) thickeners (viscosity control agents); (7) preservatives; (8) colorants (coloring agents); and (9) pH adjusters. These ingredients are well known to those skilled in the art. Those skilled in the art will appreciate that other ingredients can be used for their known intended use in the compositions of this invention, and such ingredients can be selected from those known in the art in accordance with the teachings herein, and such selection can be made without the need for undue experimentation.

An alternative embodiment of the invention employs a density increaser mixed into otherwise low density beads (relative to the intended suspension medium) to increase the density of the beads so that the beads maintain an approximately uniform spatial distribution in a liquid medium. The inventive beads would comprise a structural bead material and a density-increasing agent within the beads in a quantity effective to prevent migration of the gel beads in a liquid medium. The density increaser can comprise any material that has a density greater than 1 g/ml. The size of density increaser particulate should be smaller than the size of gel beads. Preferred fillers have an average particle size less than about 20-100 microns. In many embodiments, average particle size preferably should be less than 50 microns, and more preferably about 10 microns.

The ability to the adjust the density of beads is useful in a suspension comprising beads of different densities where beads having a density greater than the suspension medium would over time migrate to the bottom while beads having a density less than the density of the suspension medium would migrate to the top. An alternative embodiment of the invention employs a set of beads comprising density reducer and another set of beads comprising density increaser to adjust the respective densities of the beads to be close to the density of the suspension medium.

For example, a dense body cream has suspended within a first set of high density beads which comprise an exfoliant and other high density ingredients and a second set of low density beads containing for example a low density moisturizer. The result is a suspension where over time, the first set of beads migrate to the bottom of the container while the second set of beads migrate to the top of the container. By employing the inventive method, for that first set of beads, a density reducer is mixed in during the formulation while a density increaser such as cosmetic clay or some other dense particulate matter is mixed into the second bead formulation a density increaser. The resulting suspension maintains a more uniform distribution of both sets of beads in the cream over time.

It is also contemplated that the above method can be applied to beads comprising plastic materials such as polyethylene or wax. The above compositions and methods can also be applied to non-cosmetic products such as foodstuffs, home decorations, pharmaceuticals and other suitable applications.

Accordingly, the invention can provide, in preferred embodiments, density controlled gel beads, that can serve as an aesthetically appealing cosmetic carrier for topically applied active agents and can be uniformly and stably distributed in a suitable liquid medium, while being suitable for formulation in traditional cosmetic vehicles providing novel and useful consumer and other products. The inventive density controlled gel beads can protect labile and other actives such as botanical extracts, desquamating enzymes, exfoliants, vitamins and the like, and deliver such agents to the skin in active form. The density-controlled gel beads can also serve as cosmetic or pharmaceutical delivery systems which offer separation of active ingredients from formulation ingredients and which can maintain that separation through typical formulation processes, while maintaining adequate product consistency and uniformity and a desirable aesthetic appearance in its packaging, at the point of purchase and during use. Such beads may survive modest elevated processing temperatures and emulsification processes and provide controlled release of actives at a delivery point, optionally permitting localized concentration of actives at the delivery point.

Furthermore, employment of expansible hollow microspheres for density control in the described inventive products enables desired control to be achieved with little impact on the final product and little adverse impact in use. In many instances, the small particles will not be apparent, e.g. on the skin, or may have a useful lubricating or other effect.

The inventive products and processes lend themselves to the creation of novel products. For example blue density controlled gel beads may be uniformly dispersed in a yellow liquid medium providing an attractive, color-coordinated green-and-yellow appearance in the container. When topically applied, the blue of the beads becomes apparent on the skin or other surface, drawing attention to the bead material and possibly to an active or actives contained therein. Other interesting color combinations will be apparent to those skilled in the art.

In addition to cosmetics, pharmaceuticals and the like, the inventive compositions and methods can also provide novel foodstuffs, for example, a novel oil-and-vinegar salad dressing. Known oil and vinegar based dressings are packaged in bottles wherein the vinegar, herbs and spices settle to the bottom while the oil floats on top, resulting in an unappealing looking dressing. The user must then shake the bottle to mix the oil, vinegar, herbs and spices before use. To combat this problem, there are dispensers which hold the oil and the vinegar in two separate compartments to be mixed as they are poured through a common spout. However, the ratio of oil to vinegar is difficult to control and such dispensers are bulky and expensive to manufacture.

Pursuant to an alternative embodiment of the invention, one or more of the oil, herbs and spices can be suspended inside density controlled particles or gel beads. For example, herbs and/or spices could be contained in gelatin beads of cheese or other bead forming foodstuff, containing heat expandable microspheres. The microspheres could comprise thermoplastic starch, expanded starch, a resilient polysaccharide, cellulose or other ingestible shell material containing an innocuous gas for example carbon dioxide, air or nitrogen to reduce the bead density to about that of vinegar. The coating of particles 10 could further be colored or opaque to enhance the effect. Because of the nearly uniform density of the product, when the user poured the dressing onto the salad, he would taste the oil, vinegar, and spice in every bite. The improved product could still use conventional packaging while having an enhanced visual effect and an enhanced flavor experience for the taster. In an alternative embodiment, the method could be used to make herb flavored oils where the herbs are contained within density controlled particles rather than merely settled at the bottom of the bottle. Of course, care would be taken to select appropriate materials to make particles 10 from materials which are safe and edible. Heat resistance would be taken into account as well. In the case of the flavored oil, it may be advantageous to have the particle coating dissolve at a certain temperature so that the mixture of oil and spice is realized in the taster's mouth.

The entire disclosure of each patent and patent application cross-referenced or referenced herein and of each non-patent publication referenced herein is hereby incorporated herein by reference thereto, as though wholly set forth herein. Each document incorporated by reference in any of the foregoing patents, patent applications or non-patent publications is also incorporated herein in its entirety by reference thereto.

While some illustrative embodiments of the invention have been described above, it is, of course, understood that various modifications will be apparent to those of ordinary skill in the art. Such modifications are within the spirit and scope of the invention, which is limited and defined only by the appended claims.

The invention claimed is:

1. A method of preparing density-controlled beads dispersible in a liquid medium for incorporation into cosmetic products, with the beads comprising as ingredients:
   (i) an active agent;
   (ii) an effective quantity of a density-control agent that reduces the density of the resulting beads to promote uniform dispersion in the liquid medium by providing the bead with a desired bulk density; and
   (iii) a gelling agent that is liquid at elevated temperatures, the method comprising:
      (a) dissolving the gelling agent in water at an elevated temperature sufficient to dissolve the gelling agent to form a first mixture, the gelling agent being dissolved in a proportion of gelling agent to water effective to form a gel at a lower temperature than the elevated temperature;
      (b) dispersing the density-control agent in water or oil at room temperature to form a second mixture;
      (c) adding the second mixture to the first mixture to form a third mixture;
      (d) cooling the third mixture to a discharge temperature below the elevated temperature but above the gelling point of the first mixture;
      (e) discharging the third mixture through a needle to form droplets or globules, the third mixture being discharged while at the discharge temperature; and
      (f) cooling the droplets or globules to form beads.

2. A method according to claim 1 wherein cooling the droplets or globules includes exposing the drops to a liquid maintained at a temperature below the third mixture's gelling point, whereby the drops are formed into gel beads incorporating the density-reducing agent.

3. A method according to claim 1 wherein the gel beads have an average particle diameter of from about 0.1 mm to 10 mm, and said water soluble gelling agent comprises agar, and wherein said carrier comprises water and said liquid to which said drops are exposed is hydrophobic.

4. A method according to claim 3 wherein the first temperature is about 90° C.

5. A method according to claim 1 wherein a water-soluble restraining polymer is included in the gel beads and wherein said carrier comprises water and said liquid to which said drops are exposed is hydrophobic.

6. A method according to claim 5 wherein an active agent is added into said first, second, or third mixture and wherein said carrier comprises water and said liquid to which said drops are exposed is hydrophobic.

7. A method according to claim 6 wherein the restraining polymer used has a molecular weight of at least 50,000 daltons and is effective to prevent egress of the restraining polymer from the gel, the restraining polymer having retention groups to bind the active agent to the restraining polymer for retention in the gel beads, being present in a proportion effective to deliver an effective amount of the active agent and being selected from the group consisting of polyquaternium 11, polyquaternium 24, laurdimonium hydroxyethylcellulose, cocodimonium hydroxyethylcellulose, steardimonium hydroxyethylcellulose, quaternary ammonium substituted water-soluble polysaccharides, alkyl quaternary celluloses and polypeptides having or provided with retention groups to retain the active agent.

8. A method according to claim 6 wherein the gel beads are manually crushable on the skin to increase the surface area of the gel particles and expose the restraining polymer to a topical body surface for release of the active agent.

9. A method according to claim 7 wherein the gel beads comprise about 0.2 to about 7.5% by weight restraining polymer based on the weight of the gel beads.

10. A method according to claim 1 wherein the discharge temperature is about 45° C.

11. A method according to claim 1 wherein the density-control agent is pre-dispersed in oil.

12. A method according to claim 1 comprising admixing the active agent in step (a) or step (b) whereby the active agent is incorporated in the gel beads.

13. A method according to claim 1 wherein the density-control agent comprises heat-expandable microspheres.

14. A method according to claim 1 comprising pre-dispersing a pigment in water and mixing the pre-dispersed pigment with the second mixture before adding the second mixture to the third mixture.

15. A method according to claim 1 wherein the gel beads comprise about 1.5 by weight gelling agent based on the weight of the gel beads.

16. A method according to claim 1 wherein the gel beads comprise about 0.01% to about 5% by weight density-control agent based on the weight of the gel beads.

17. A method according to claim 1 wherein the gel beads comprise about 0.02% to about 0.1% by weight density-control agent based on the weight of the gel beads.

18. A method according to claim 6 wherein the density-control agent comprises a plurality of hollow particles, wherein said plurality of hollow particles comprise a gas within a spherical shell, wherein the gas remains within the spherical shell unless said shell is ruptured.

19. A method according to claim 18 wherein the plurality of hollow particles used are gas-filled thermoplastic microspheres.

20. A method according to claim 1, wherein the density-control agent is dispersed in a quantity sufficient to give the particles a bulk density of from about 0.8 g/ml to about 0.1 g/ml.

21. A method according to claim 1, wherein the density-control agent is dispersed in a quantity sufficient to give the particles a bulk density less than or equal to the liquid medium.

22. A method as in claim 1, wherein the density-control agent used comprises hollow particles.

23. A method of preparing density-controlled beads dispersible in a liquid medium for incorporation into cosmetic products, comprising:
(a) mixing an active agent and a bead material that is liquid at elevated temperatures, said bead material comprising a restraining polymer;
(b) distributing said restraining polymer throughout said bead material;
(c) adding a density reducer to the resultant mixture, the density reducer comprising entrapped gas within a material defining a hollow particle which retains said gas unless said material is ruptured, said density reducer being introduced into the mixture in a quantity sufficient to provide a desired gel bead density;
(e) forming the resultant mixture into droplets or globules with the density reducer encapsulated therein; and
(f) cooling the droplets or globules to form beads.

24. A method as in claim 23, wherein the density-control agent used comprises hollow particles.

25. A method of preparing density-controlled beads dispersible in a liquid medium for incorporation into cosmetic products, comprising:
(a) mixing an active agent and a bead material that is liquid at elevated temperatures, said bead material comprising a restraining polymer;
(b) distributing said restraining polymer throughout said bead material;
(c) adding a density reducer to the resultant mixture, the density reducer comprising entrapped gas within a temperature-sensitive expandable thermoplastic microsphere;
(d) controlling the density and volume of said density reducer by adjusting the temperature during mixing of said expandable thermoplastic microsphere;
(e) forming the resultant mixture into droplets or globules with the density reducer encapsulated therein; and
(f) cooling the droplets or globules to form beads.

26. The method of claim 2, wherein said carrier comprises water and said liquid to which said drops are exposed is hydrophobic.

* * * * *